United States Patent
Field et al.

[19]

[11] Patent Number: 5,832,053
[45] Date of Patent: Nov. 3, 1998

[54] INSPECTION CELL

[75] Inventors: Kenneth Malcolm Field; Mark Simon Finney; Trevor Anthony Nunn, all of Oxon, Great Britain

[73] Assignee: Oxford Analytical Instruments Limited, Witney, Great Britain

[21] Appl. No.: 907,142

[22] Filed: Aug. 6, 1997

[51] Int. Cl.⁶ .................................................. G01N 23/223
[52] U.S. Cl. .................................................. 378/45; 378/79
[58] Field of Search ................................. 378/44–49, 79, 378/208

[56] References Cited

U.S. PATENT DOCUMENTS 4,154,533  5/1979  Levine .
4,640,614  2/1987  Roberts et al. .
5,162,103  11/1992  Dechene et al. .
5,272,745  12/1993  Smallbone .
5,591,461  1/1997  Komatsu et al. .

*Primary Examiner*—Craig E. Church
*Attorney, Agent, or Firm*—Price, Gess & Ubell

[57] ABSTRACT

A powder sample inspection cell assembly comprising a cell, an aperture being provided in a side wall of the cell; a closure member which can be clamped over the aperture to close it; and means for compacting the contents of the cell, the cell being oriented such that, after compaction, powder in the cell is sufficiently compacted so as not to escape through the aperture when the closure member is removed.

13 Claims, 2 Drawing Sheets

INSPECTION CELL

FIELD OF THE INVENTION

The invention relates to an inspection cell, particularly for use with powder samples.

DESCRIPTION OF THE PRIOR ART

The analytical control of powdered raw materials used in automated process lines is of primary importance in many industries and X-ray fluorescence (XRF) instruments have been used for this purpose for many years. Traditionally, this has been done by taking discrete samples from the process line and analysing them at a remote central control laboratory. This procedure is able to give very reliable results but is unable to monitor changes between sampling periods. The increasing costs of manning three shift operations and the large stockpiles of raw materials required to keep the process within the required tolerance is creating severe problems for industry throughout the world. The elevation of these problems requires more frequent analysis than is current practice. This requirement leads naturally to "on-line" analysis, where samples are taken automatically and analysed with as high a frequency as possible.

Future process plants are expected to become more automated and it is envisaged that the most advanced will operate without laboratory back-up using only "on-line" systems for analytical process control. This will create a demand for "on-line" XRF analysers of very high precision, accuracy and reliability and will probably mandate switchable duplicate systems to achieve 99.7% availability.

"On-line" analysis of powders using XRF is described in Carr-Brian, K. G., Kipping, P. J., New, R., Nutter, J. C., and Thomlinson, F. J., World Cement Technol. 8(4) (1977) 2–8; and Carr-Brian, K. G., X-ray Analysers in Process Control, Elsevier Applied Science, London and New York, 1989, pp. 71–97.

However, many problems must be overcome before such systems can be fully utilised. In particular, the formation of a flat, homogenous sample so that XRF analysis can be carried out with confidence. Many methods have been used to form uniform samples including conveying the powder on a horizontal belt to a sample forming "shoe" and thence onto the analysis head as described in the papers mentioned earlier. Vertical delivery to the analyser has been achieved, mainly for liquid slurries, by the use of a closed flow cell, however, this requires the use of a suitable X-ray transmitting window (normally made from very thin plastic) in order to contain the sample material and to allow analyte X-rays through to the detection system. This approach creates its own problems, namely the window seriously attenuates analyte X-rays from low atomic number elements reducing analytical sensitivity. Also, powder may stick to the window creating memory effects between analyses. Many powders will be delivered at high temperature and their general coarse and abrasive nature will lead to changes in the X-ray attenuation properties of the window as it wears and ultimately to its destruction.

SUMMARY OF THE INVENTION

In accordance with the present invention, a powder sample inspection cell assembly comprises a cell, an aperture being provided in a side wall of the cell; a closure member which can be clamped over the aperture to close it; and means for compacting the contents of the cell, the cell being oriented such that, after compaction, powder in the cell is sufficiently compacted so as not to escape through the aperture when the closure member is removed.

We have realised that it is possible to take advantage of the natural compaction affect which is achievable with powder samples, particularly cement samples, to allow the sample to be viewed without any intermediate wall. This then overcomes the problems mentioned above concerning attenuation.

Typically, the cell will be positioned in an upright manner, preferably substantially vertically. Off-vertical orientations are also possible provided sufficient compaction is achievable.

Preferably, the closure member has a smooth, inwardly oriented face. The compacted powder will then take up a corresponding surface formation which is particularly useful for applications such as XRF.

The closure member could be completely separable from the cell but preferably the closure member is mounted to the cell for movement between open and closed positions. For example, the closure member could be pivoted to the cell. This mounting may be direct to the cell wall or indirect to a support which is connected to the cell.

Powder can be supplied and removed from the cell in a variety of ways. For example, a single opening could be provided for both supplying and removing powder, the cell being inverted to allow powder to be removed. More conveniently, a separate, upper inlet and lower outlet are provided in the cell. One or both of these could be provided in a side wall of the cell but preferably are opposite axial openings of the cell.

The lower outlet is conveniently closed by a valve such as a pinch valve.

The means for compacting the contents of the cell may comprise a ram which presses the contents of the cell against the pinch value. However in a preferred embodiment the means for compacting the contents of the cell comprises a vibrator coupled to the cell. This arrangement has less mechanical moving parts and lends itself more easily to the frequent measurements required for "on-line" analysis.

In order to allow the cell to vibrate, it is preferably connected via a resilient device, for example one or more springs or rubber mounts, to a base plate.

The vibrator can be any form of conventional vibrating device but conveniently comprises a rotating ball vibrator. Alternatively the vibrator may comprise a motor connected to rotate an out of balance mass supported on the cell. In this case, both the motor and the out of balance mass are typically supported on the cell. In a further alternative the vibrator may comprise a turbine type vibrator.

In a preferred embodiment the inner surface of the side wall of the cell adjacent the aperture has an angled portion below the aperture to facilitate the easy removal of the contents of the cell after compaction. For example the aperture may be defined by an annular plate constructed with steep internal sides.

The invention can be used with any type of inspection system where the surface of a powder material is to be inspected. These will typically analyse the constituents of the sample but could monitor other properties such as colour. The invention is particularly suitable, however, for use with XRF. Thus, we provide X-ray fluorescence inspection apparatus comprising an inspection cell according to the invention; and an X-ray fluorescence analyser which can be positioned to inspect a powder sample exposed through the open aperture. Typically, the analyser is movable between the inspection position and a retracted position spaced from the aperture. This then allows the closure member easily to be mounted over the aperture.

BRIEF DESCRIPTION OF THE DRAWINGS

An example of X-ray fluorescence inspection apparatus incorporating a powder sample inspection cell according to the invention will now be described with reference to the accompanying drawings, in which.

EMBODIMENT

Figure 2:
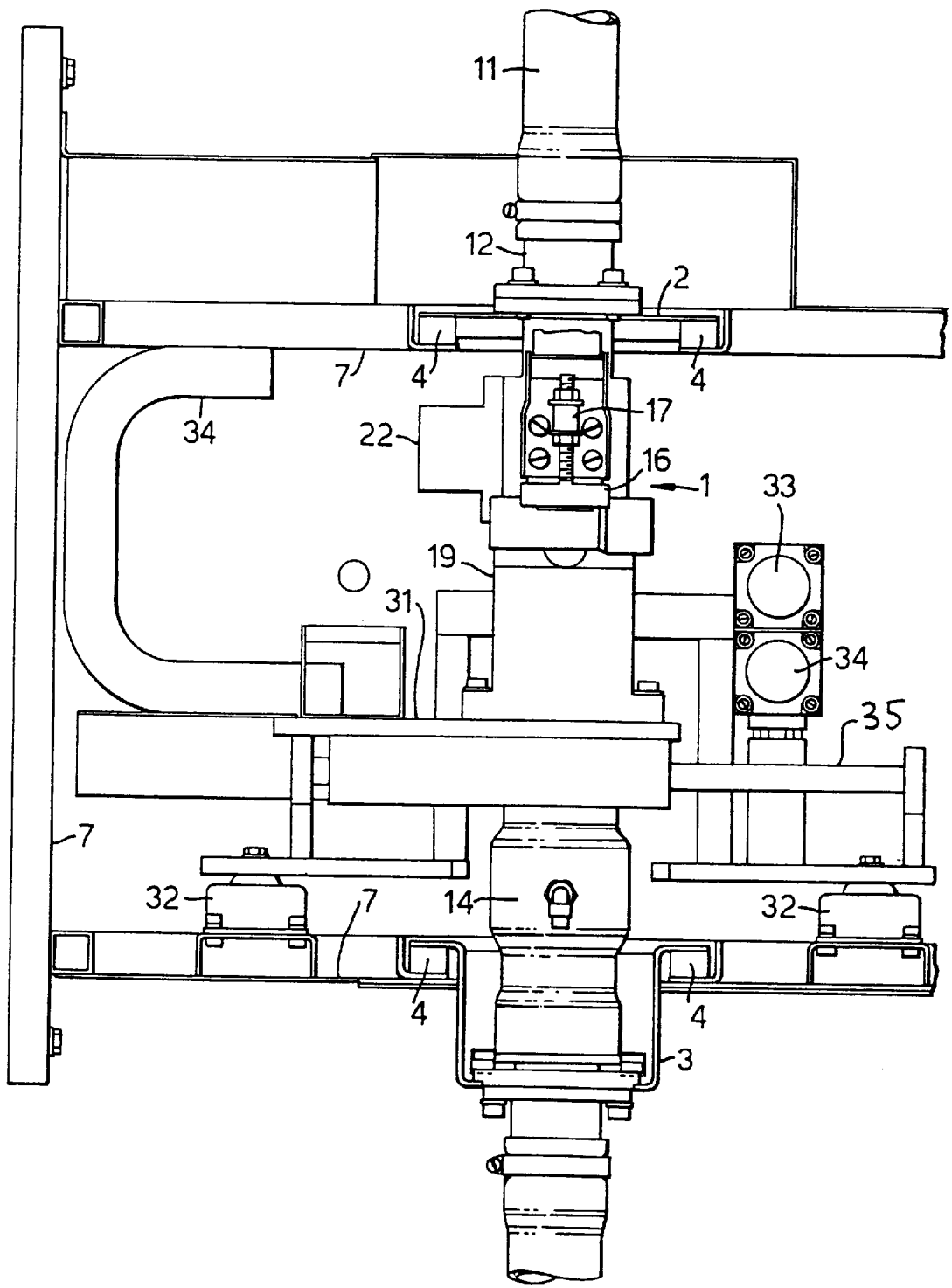

The apparatus shown in the drawings comprises a tubular cell 1 having an internal diameter of about 40 mm and an axial length of 40–50 cm. The interior of the cell defines a sample inspection chamber 36. As can be seen in FIG. 2, the cell is connected to a pair of upper and lower support flanges 2,3 which are mounted on a base frame 7 via flexible rubber mounts 4. The flexible rubber mounts 4 allow the cell to vibrate, in particular from side to side.

The cell 1 has an upper opening 10 connected to a feed tube 11 which in turn is connected to a main process stream (not shown) via a control valve (also not shown). A flow detector (not shown) in position 12 such as a light source and light detector monitors for the passage of material through the feed tube 11 and controls the position of the valve connected to the main process stream so as to meter the supply of material.

The cell 1 also defines an outlet opening 13 at its base which is connected with a pinch valve 14. The pinch valve 14 can be actuated to close and open the opening 13.

A circular aperture 15 having a diameter in the range 10–20 mm, typically about 18 mm is provided in a side wall of the cell 1. The aperture can be selectively closed by a 40 mm diameter, polished tungsten carbide circular cover 16 pivoted via a clamp 17 to the cell 1. A pneumatic cell window closure mechanism 18 pivots the tungsten carbide cover 16 from an open position 5 to a closed position 6 in which it is clamped across the aperture 15.

A conventional XRF analysis head 19 is slidable into an analysis position shown in FIG. 2 and a retracted position (not shown) in which the cover 16 can be pivoted to its closed position. The head 19 is mounted on a carriage 31 slidably mounted to a rail 35 which is mounted on base frame 7 via four rubber shock proof mounts 32 (only two of which are shown in FIG. 2).

The shock proof mounts 32 decouple the frame 31 from the vibrating cell 1, ensuring that the analysis head 19 is not vibrated. Signals are transmitted to and from the analysis head 19 via cable 34.

In order to locate the cell 1 accurately with respect to the analysis head 19, a cell clamp 20 is slidably positioned on the base plate 7, the clamp having a protrusion 21 which will locate in a corresponding recess 30 in the wall of the cell 1. The dimension of the recess 30 will allow the cell 1 to vibrate.

Vibration is achieved by operating a rotating ball vibrator 22 mounted to the cell 1. The vibrator 22 is a K-series ball vibrator (model K-13) manufactured by Vibratechniques Ltd. The frequency is controlled by compressed air typically 18000 r.p.m. at 2 bar input pressure.

In operation, a controller (not shown) connected to the flow detector, the vibrator 22, the pneumatic actuator 18 and the analysis head 19 opens the valve connected to the main process stream. This diverts a sample of the powder material from the main process stream into the feed tube 11 past the flow detector. When the flow detector senses the passage of the powder, this information is notified to the controller which will initiate a timer which, when timed out, will cause the inlet valve to close. This will correspond to the supply of sufficient powder material to the cell 1.

At this stage, the tungsten carbide cover 16 is clamped over the aperture 15 and the pinch valve 14 is closed. Thus, powder will build up within the cell 1.

Once the cell 1 has been filled, the vibrator 22 is actuated causing the cell 1 to vibrate and the powder to compact. The speed of the motor can be varied in order to change the frequency of vibration. A typical frequency is 10 kHz, and a typical compaction time is 20–30 seconds. The dominant mode of vibration of the cell 1 is horizontal (i.e. transverse to the direction of travel of the powder material in the cell).

After compaction, the cover 16 is unclamped and moved away to expose the sample surface ready for analysis. The polished surface of the cover 16 ensures that the sample surface contained in the aperture 15 is flat after compaction.

Figure 1:
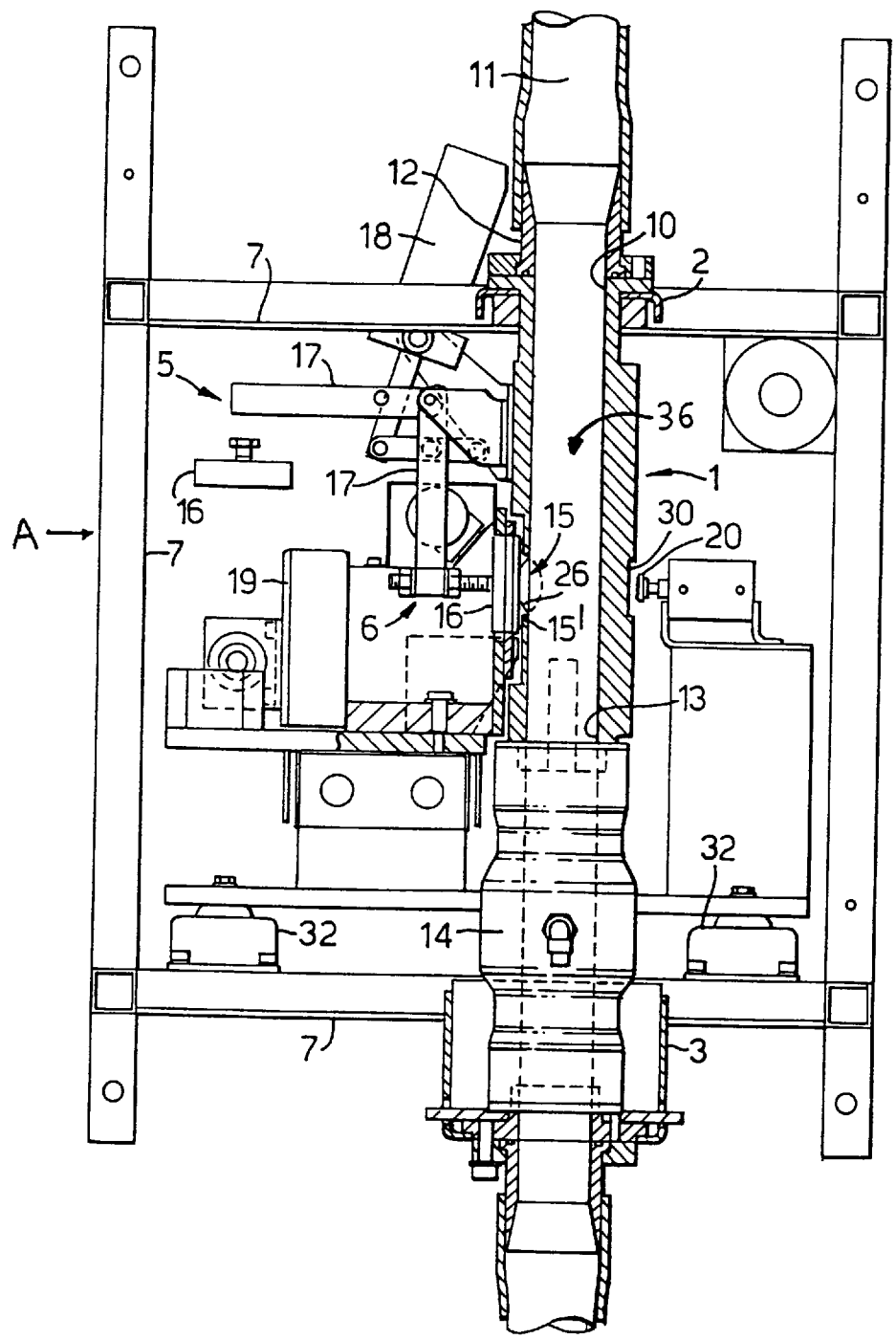
FIG. 1 is a schematic, part-longitudinal section through the apparatus showing the aperture cover in open and closed positions; and, FIG. 2 is a schematic side elevation in the direction A in FIG. 1.

The analyser head 19 is then moved into the fixed sample position shown in FIG. 1 and 2 so that XRF analysis can take place.

Once the analysis has taken place, the analyser head 19 is moved away from the aperture 15 into its retracted position where stabilisation routines can take place to check the stability of the analysis system. In its retracted position the analysis head is in line with two pure metal targets 33,34 to enable conventional calibration techniques to be carried out.

The tungsten carbide cover 16 is clamped back over the aperture 15 and the pinch valve 14 is opened to allow the powder to escape. Optionally, the cell 1 can be vibrated (typically at 10 kHz for 20–30 seconds) to encourage the sample of powder material to drop out of the cell 1. An annular plate 15' defining the aperture 15 is constructed with steep internal sides 26 to facilitate the easy removal of the sample under vibration. The pinch valve 14 is then closed and the cell is ready to receive the next head of powdered sample. The plate 15' has side flanges (not shown) which wrap around the tubular cell 1.

The windowless flow cell approach works because the tungsten carbide cover presses up against the aperture 15 during filling, compaction and emptying and does not allow any powder to escape into the main body of the analyser. Compaction of the powder provides enough cohesion to allow the material to support itself in the aperture once the cover is removed.

The system described above has been successively used to determine the concentration of $Al_2O_3$, $SiO_2$, CaO and $Fe_2O_3$ in cement raw meal powder. The typical total measurement time, i.e. sample preparation and analysis, was 150 seconds, 60 seconds of which was preparation time.

We claim:

1. A powder sample inspection cell assembly comprising a cell having a side wall, an aperture being provided in said side wall of said cell; a closure member which can be clamped over said aperture to close it; and means for compacting the contents of said cell, said cell being oriented such that, after compaction, powder in said cell is sufficiently compacted so as not to escape through said aperture when said closure member is removed.

2. An assembly according to claim 1, wherein said closure member has a smooth, inwardly oriented face.

3. An assembly according to claim 1, wherein said closure member is mounted to said cell for movement between open and closed positions.

4. An assembly according to claim 3, wherein said closure member is pivoted to said cell.

5. An assembly according to claim 1, wherein said cell has an upper inlet and a lower outlet for said powder.

6. An assembly according to claim 5, wherein said outlet is closed by a valve, for example a pinch valve.

7. An assembly according to claim 1, wherein said cell is connected via a resilient device to a base plate.

8. An assembly according to claim 1, wherein said means for compacting the contents of said cell comprises a vibrator coupled to said cell for vibrating the contents of said cell.

9. An assembly according to claim 1, wherein said cell is positioned in an upright manner, preferably substantially vertically.

10. An assembly according to claim 1, wherein said cell is tubular.

11. An assembly according to claim 1, wherein an inner surface of said side wall of said cell adjacent said aperture has an angled portion below said aperture to facilitate the easy removal of said contents of said cell after compaction.

12. X-ray fluorescence inspection apparatus comprising an inspection cell assembly comprising a cell having a side wall, an aperture being provided in said side wall of said cell; a closure member which can be clamped over said aperture to close it; and means for compacting the contents of said cell, the cell being oriented such that, after compaction, powder in said cell is sufficiently compacted so as not to escape through said aperture when said closure member is removed; and an X-ray fluorescence analyser which can be positioned to inspect an exposed powder sample through said open aperture of said cell.

13. Apparatus according to claim 12, wherein said X-ray fluorescent analyser is movable between an analysis position located adjacent said aperture and a retracted position spaced from said aperture.

* * * * *